(12) United States Patent
Mohammed et al.

(10) Patent No.: US 8,383,949 B2
(45) Date of Patent: Feb. 26, 2013

(54) METHOD TO FORM LATERAL PAD ON EDGE OF WAFER

(75) Inventors: Edris M. Mohammed, Beaverton, OR (US); Hinmeng Au, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 349 days.

(21) Appl. No.: 12/649,328

(22) Filed: Dec. 29, 2009

(65) Prior Publication Data

US 2011/0155435 A1   Jun. 30, 2011

(51) Int. Cl.
*H05K 1/03* (2006.01)
*H05K 1/00* (2006.01)
*H05K 1/11* (2006.01)
*H05K 7/10* (2006.01)
*H05K 1/18* (2006.01)
*H01L 23/58* (2006.01)
*H01L 23/04* (2006.01)
*H01L 23/48* (2006.01)

(52) U.S. Cl. ........ 174/255; 174/250; 174/261; 257/650; 257/730; 257/734; 361/767; 361/778

(58) Field of Classification Search .................. 174/250, 174/255, 260; 257/650, 730, 734, E23.01, 257/786; 361/767, 772, 778, 779
See application file for complete search history.

(56) References Cited

U.S. PATENT DOCUMENTS

| 5,682,674 | A | * | 11/1997 | Yamazaki et al. | 29/830 |
| 6,235,551 | B1 | | 5/2001 | Farnworth et al. | |
| 6,410,859 | B1 | * | 6/2002 | King | 174/260 |
| 6,414,374 | B2 | * | 7/2002 | Farnworth et al. | 257/620 |
| 6,800,942 | B1 | * | 10/2004 | Kinsman | 257/777 |
| 7,535,109 | B2 | | 5/2009 | Robinson et al. | |
| 7,632,749 | B1 | | 12/2009 | Ogawa et al. | |
| 2002/0031857 | A1 | * | 3/2002 | Kinsman | 438/107 |
| 2007/0045837 | A1 | | 3/2007 | Shindo et al. | |
| 2008/0315409 | A1 | * | 12/2008 | Cordes et al. | 257/737 |

FOREIGN PATENT DOCUMENTS

WO   2011/090572 A2   7/2011
WO   2011/090572 A3   11/2011

OTHER PUBLICATIONS

International Search Report and Written Opinion received for PCT Application No. PCT/US2010/059315, Mailed on Sep. 15, 2011, 10 pages.
International Preliminary Report on Patentability received for PCT Patent Application No. PCT/US2010/059315, mailed on Jul. 12, 2012, 2 pages.

\* cited by examiner

*Primary Examiner* — Timothy Thompson
*Assistant Examiner* — Sherman Ng
(74) *Attorney, Agent, or Firm* — Kevin A. Reif

(57) ABSTRACT

Embodiments are directed to an apparatus and fabrication method to form pad arrays on the edge of a substrate wafer substrate. Embodiments of the invention make it possible for surface mount devices to be bonded vertically (i.e. on their side) using standard semiconductor assembly processes.

8 Claims, 4 Drawing Sheets

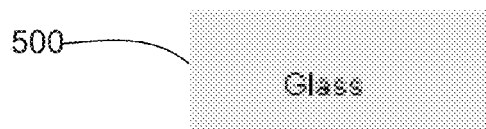
Fig. 5A Fig. 5B
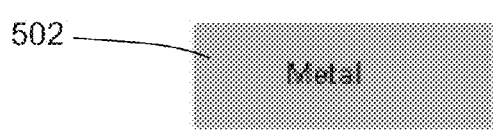
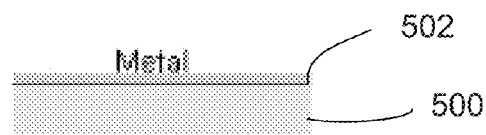
Fig. 6A Fig. 6B
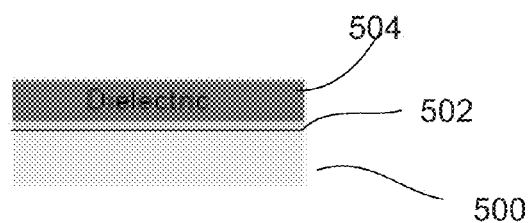
Fig. 7A Fig. 7B
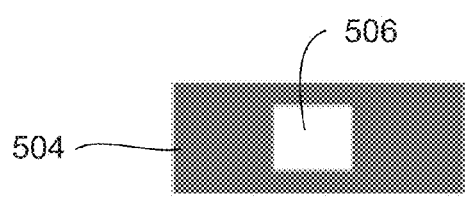
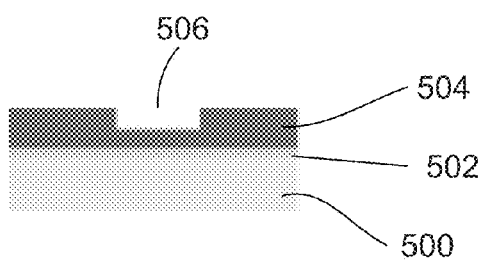
Fig. 8A Fig. 8B

METHOD TO FORM LATERAL PAD ON EDGE OF WAFER

FIELD OF THE INVENTION

Embodiments of the present invention are directed to surface mounting technology and, more particularly, to forming pads on the edges of a substrate.

BACKGROUND INFORMATION

Embodiments of the invention relate generally to surface mounting technology utilized to electrically and physically interconnect electronic components. In surface mount technology (SMT), two surfaces may be electrically interconnected using solder bumps or balls that are deposited upon one of the surfaces and then reflowed or heated to solder the two surfaces together. SMT may be an advantageous process because it may not be necessary to work in the region between the two surfaces to be joined and because a large number of components may be connected in the same reflow step.

Sometimes, for example in the case of electro-optical components, it may be desirable to vertically bond (i.e. mount on its side) a component to a substrate. FIG. 1 is an example of vertical bonding a component 100 to a substrate 102. The component 100 may be a laser, a photodiode, or any component to be vertically mounted. In this case, the component is an opto-electrical component which may typically comprise a metal layer 104, a dielectric layer 106, and a transparent glass or plastic portion 108.

During fabrication of the component 100, the metal layer 104 may be the bottom of the component 100 and the glass/plastic layer 108 may be the top. The bottom metal layer 104 may comprise a corner bonding pad 110 projecting upward from the metal layer 102 near the top edge of the component 100. The pad 110 may be for making electrical connections as well as mechanical attachment via a solder bump 112 to the substrate 102 when the component 100 is flipped on its side, as shown.

While one pad 110 is shown in FIG. 1, a plurality of such pads may be present to provide corner solder joint arrays used as a means to electrically interface with I/O, power and bias bumps, for example on a microprocessor package. Potential problematic issues of this type of solder joint and contact pad may be manufacturability compatibility with the standard flip chip process. For example, it may be difficult for a pick and place tool to automate the placement of the component on the substrate. Other issues may include proper solder reflow and self alignment difficulties. Mechanical robustness of the finished product and potential reliability issues may arise because the joint may be sheared off at elevated temperatures.

BRIEF DESCRIPTION OF THE DRAWINGS

The foregoing and a better understanding of the present invention may become apparent from the following detailed description of arrangements and example embodiments and the claims when read in connection with the accompanying drawings, all forming a part of the disclosure of this invention. While the foregoing and following written and illustrated disclosure focuses on disclosing arrangements and example embodiments of the invention, it should be clearly understood that the same is by way of illustration and example only and the invention is not limited thereto.

FIGS. 5A-11A and 5B-11B are top and side views, respectively, illustrating the processing steps for forming a component having lateral contact pads according to one embodiment of the invention.

DETAILED DESCRIPTION

Described is an apparatus and fabrication method to form pad arrays on the edge of a substrate wafer substrate. Embodiments of the invention make it possible for surface mount device components to be bonded vertically using standard semiconductor assembly processes.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
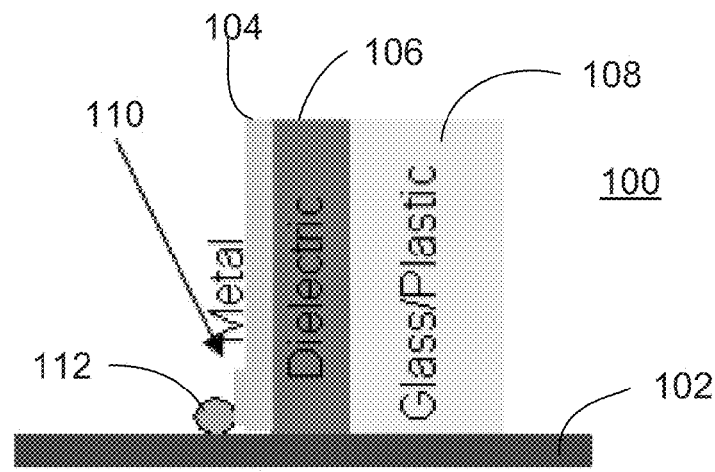
FIG. 1 is a side view of a typical way in which a device may be vertically mounted to a substrate.
Figure 2:
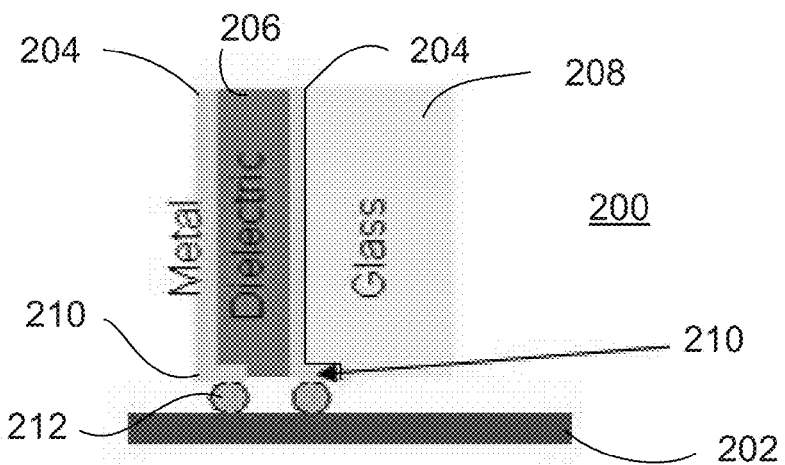
FIG. 2 is a side view of one embodiment of the inventive component having lateral contact pads being flipped on its side and vertically mounted to a substrate.

Referring now to FIG. 2, there is a side view of one embodiment of the invention which may comprise a component 200 to be vertically mounted on its side to a substrate 202 by flip-chip techniques. The component 200 may comprise a dielectric layer 206 and a glass or plastic layer 208 and may also comprise one or more metal layers 204. The metal layer 204 may comprise a conductive trace running along the dielectric material 206 and may comprise a pad 210 generally perpendicular to the metal trace 204 which runs along the side of the device 200. In some embodiments additional metal layers or electrical traces 205 may be sandwiched between the various layers also terminating in a pad 211 running on the side of the device. The device may be electrical, optical, electro-optical or passive. The component 200 may be positioned on its side by automated pick and place machinery with the lateral pads 210 bonded to the substrate 202 by reflowing the solder bumps 212.

Figure 3:
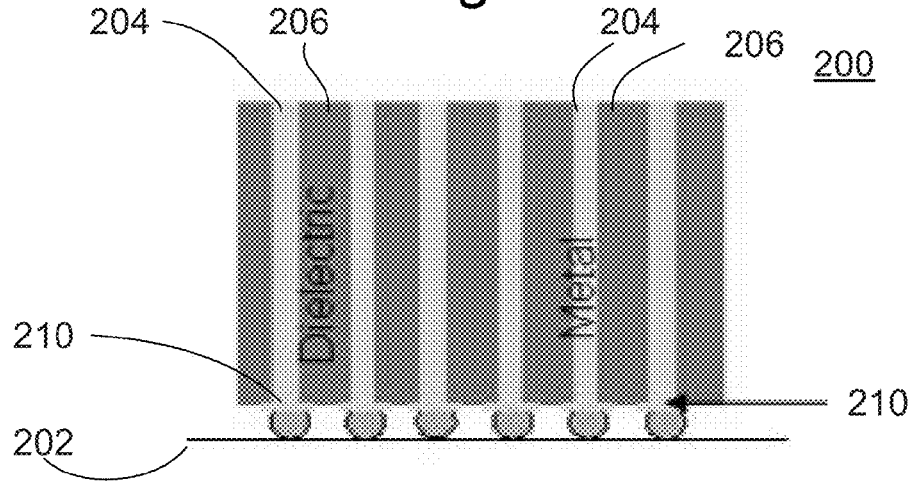
FIG. 3 is a back view of the device shown in FIG. 2.

FIG. 3 shows the back view of the device shown in FIG. 2 (the glass/plastic portion 208 facing away). The component 200 may comprise multiple metal trace layers 204 sandwiched between multiple dielectric layers 206. Each metal trace 204 may include a lateral bonding pad 210 extending onto the side of the component 200. Thus, when flipped on its side as shown, it may be connected to a substrate 202 by solder bumps 212.

Figure 4A:
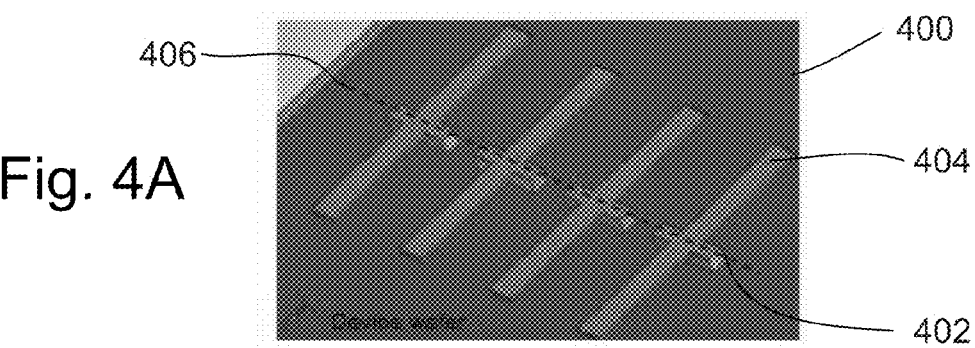
FIGS. 4A-4D are plan views of one embodiment of the invention in progressive stages of fabrication.
Figure 4B:
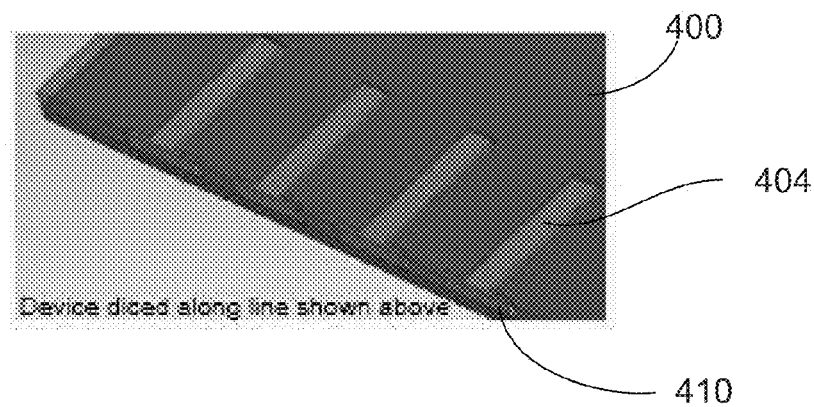
Figure 4C:
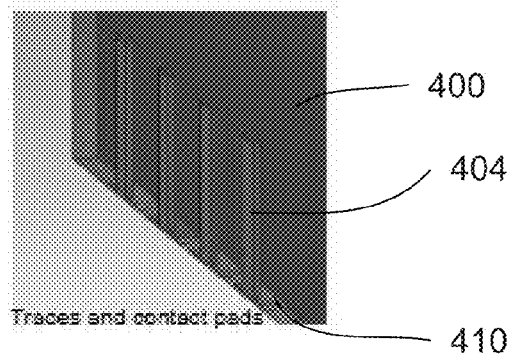

Referring now to FIG. 4A-4C there are illustrated steps for forming lateral pads, such as shown in FIG. 3. As shown in FIG. 4A, a device wafer 400 may comprise a dielectric material. One or more cavities or trenches 402 may be etched into the dielectric material 400 and filled with a metal. One or more electrical traces 404 may be deposited on the dielectric material over the filled trenches 402 and running generally perpendicular to the trenches 402. The wafer 400 may then be diced along line 406.

Figure 4D:
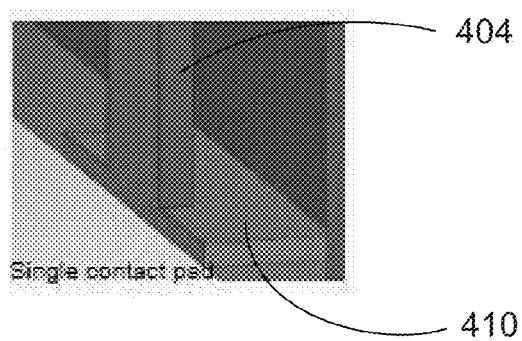

As shown in FIG. 4B, after dicing, the result is metal traces 408 with a cross-section of the metal filled trench exposed to form lateral contact pads 410. As shown in FIG. 4C, when turned on its side, the contact pads 410 may permit the resultant device to be vertically mounted. FIG. 4D shows a close-up view of one such lateral contact pad 410 and its associated trace 408.

FIGS. 5A-B to FIGS. 11A-B illustrate the processing steps for realizing lateral contact pads. The "A" figures are top views and the "B" Figures are cut-away side views of the same processing steps. Referring now to FIGS. 5A and 5B, a pre-processed glass substrate 500 may be provided. In FIGS. 6A and 6B, a metal layer 502 may be deposited, such as by sputtering to form a ground layer. In one embodiment, the metal may be copper (Cu), for example.

Figure 9A:
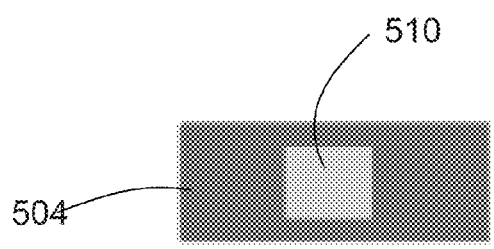
Figure 9B:
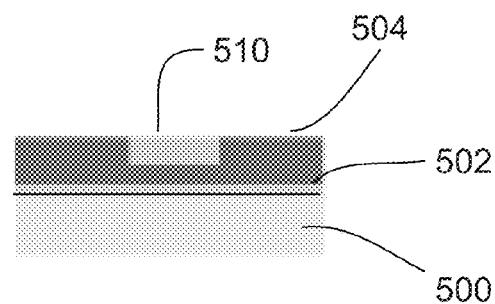

In FIGS. 7A and 7B, a dielectric layer 504 may be deposited on the metal layer 502. In one embodiment, the dielectric layer 504 may be Benzocyclobutene (BCB) on glass or some other suitable material. Referring to FIGS. 8A and 8B, a trench 506 may be etched into the dielectric layer 504. In FIGS. 9A and 9B, the cavity 506 may be filled with a metal 510, such as copper.

Figure 10A:
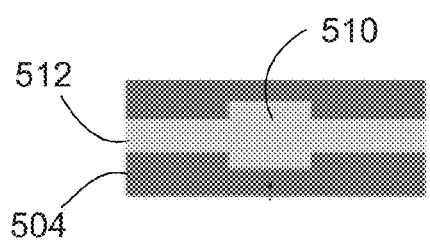
Figure 10B:
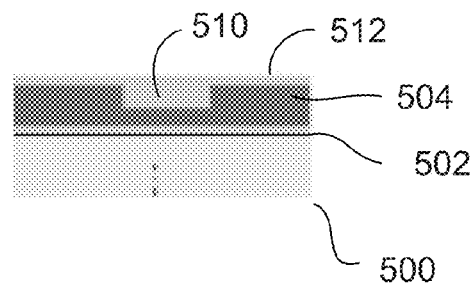
Figure 11A:
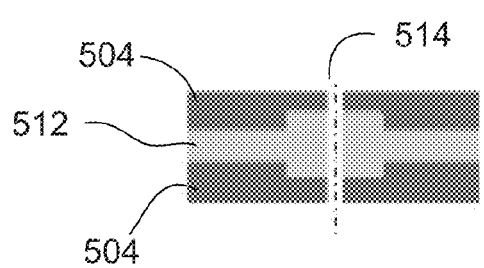
Figure 11B:
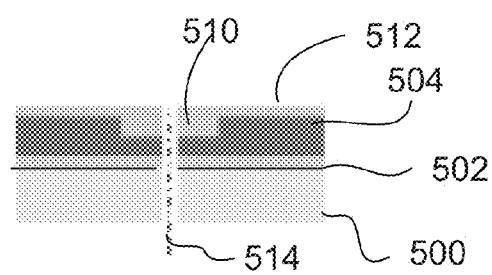

In FIGS. 10A-10B, a microstrip trace may be formed on the top surface of the dielectric layer 504. This process may be repeated many times at the wafer level to form pad arrays. Finally, as illustrated in FIGS. 11A-11B, the device may be diced along dice line through the trench 510. After dicing, the filled trenches form lateral contact pads such that when the unit is flipped on its side by 90° it may be solder mounted to a substrate as shown in FIGS. 2 and 3.

The metal traces 512 used for this particular case are microstrip transmission lines. However a stripline, coplanar waveguide or other forms of transmission line are also possible. In other embodiments, formation of multiple metal and dielectrics layers is possible.

The dicing process could be done, for example, either with a diamond saw or using laser milling. To control edge roughness during cutting certain parameters of the cutting tool may be judiciously chosen. In case of sawing the edge roughness may depend on the blade type and the saw speed. Acceptable edge roughness could be obtained by controlling these parameters. In case of laser milling several parameters are included. These are laser power (current), rep-rate, pulse duration and scanning speed. However, the pulse duration may be a strong factor to control roughness. For example using a picosecond pulsed laser surface roughness Ra of 0.2 um could be obtained. Much smoother surface may be achieved with femto-second lasers.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A component, comprising:
   a dielectric wafer portion comprising a plurality of metal filled trenches;
   a plurality of metal traces on the dielectric wafer portion crossing over the plurality of metal filled trenches;
   a lateral side of the component including an exposed cross-section of the metal filled trench, wherein the cross-section of each metal filled trench is a bonding pad when the component is turned on its side; and
   a glass layer on the dielectric wafer portion wherein the metal filled trench bonding pad is sandwiched beneath and between the glass layer and the dielectric wafer portion.

2. The component as recited in claim 1 further comprising:
   a plurality of said dielectric wafers stacked one on top of the other, wherein the cross-sections of the metal filled trenches comprise a bonding pad array.

3. The component as recited in claim 1 wherein the component is vertically flip-chip bonded to a substrate using the bonding pads.

4. The component as recited in claim 1 wherein the exposed cross-section of the metal filled trench has a roughness Ra of about 0.2 um.

5. A component, comprising:
   a dielectric wafer portion comprising a plurality of metal filled trenches;
   a plurality of metal traces on the dielectric wafer portion crossing over the plurality of metal filled trenches;
   a lateral side of the component including an exposed cross-section of the metal filled trench, wherein the cross-section of each metal filled trench is a bonding pad when the component is turned on its side; and
   a plastic layer on the dielectric wafer portion wherein the metal filled trench bonding pad is sandwiched beneath and between the plastic layer and the dielectric wafer portion.

6. The component as recited in claim 5 further comprising:
   a plurality of said dielectric wafers stacked one on top of the other, wherein the cross-sections of the metal filled trenches comprise a bonding pad array.

7. The component as recited in claim 5 wherein the component is vertically flip-chip bonded to a substrate using the bonding pads.

8. The component as recited in claim 5 wherein the exposed cross-section of the metal filled trench has a roughness Ra of about 0.2 um.

\* \* \* \* \*